(12) United States Patent
Palanker

(10) Patent No.: US 7,447,547 B2
(45) Date of Patent: Nov. 4, 2008

(54) NEURAL PROSTHESIS BASED ON PHOTOMECHANICAL DEFLECTORS AND TACTILE SENSORY CELLS

(75) Inventor: Daniel V. Palanker, Sunnyvale, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 633 days.

(21) Appl. No.: 10/778,943

(22) Filed: Feb. 13, 2004

(65) Prior Publication Data

US 2005/0131490 A1  Jun. 16, 2005

Related U.S. Application Data

(60) Provisional application No. 60/447,572, filed on Feb. 14, 2003.

(51) Int. Cl.
*A61N 1/08* (2006.01)
(52) U.S. Cl. .............................. 607/54; 607/2; 607/62; 600/552

(58) Field of Classification Search ................ 607/1, 607/2, 53, 54, 62, 88; 600/544, 587, 595, 600/552; 702/139
See application file for complete search history.

(56) References Cited

U.S. PATENT DOCUMENTS 7,001,608 B2 * 2/2006 Fishman et al. ............. 424/427

* cited by examiner

*Primary Examiner*—Kennedy J Schaetzle
(74) *Attorney, Agent, or Firm*—Lumen Patent Firm, Inc.

(57) ABSTRACT

An interface for selective excitation of a biological neural network is provided. The interface includes a microelectromechanical (MEMS) device having a deformable membrane, and a tactile-sensitive neural cell disposed on the deformable membrane. The cell on the deformable membrane senses motion or deformation of the membrane and provides a signal, responsive to membrane motion or deformation, to the biological neural network. Preferably, the deformable membrane and cell have about equal areas, to provide selective excitation. An interface array including at least two such interfaces is also provided. A retinal prosthesis interface array having, in each element of the array, a photodiode within the MEMS device for electrostatically actuating the deformable membrane is also provided. For this alternative, the cells and deformable membranes are preferably transparent.

18 Claims, 5 Drawing Sheets

NEURAL PROSTHESIS BASED ON PHOTOMECHANICAL DEFLECTORS AND TACTILE SENSORY CELLS

CROSS REFERENCE TO RELATED APPLICATIONS

This application is related to and claims priority from U.S. Provisional Application 60/447,572 filed on Feb. 14, 2003, hereby incorporated by reference.

FIELD OF THE INVENTION

The present invention relates to neural prostheses. More particularly, the present invention relates to selective excitation of a biological neural network.

BACKGROUND

Several degenerative retinal diseases that commonly lead to blindness, such as retinitis pigmentosa and age-related macular degeneration, are primarily caused by degradation of photoreceptors (i.e., rods and cones) within the retina, while other parts of the retina, such as bipolar cells and ganglion cells, remain largely functional.

Accordingly, provision of a retinal prosthesis connected to functional parts of the retina and providing photoreceptor functionality is an approach for treating blindness caused by such conditions that has been under investigation for some time. Known retinal prostheses provide either electrical stimulation of neural cells or chemical stimulation of neural cells.

However, retinal prostheses making use of electrical or chemical stimulation of neural cells typically require external (i.e., outside the eye) power and/or information supplies, because such prostheses usually require more power than is available at the retina. The requirement for an external supply is disadvantageous, since connecting an external supply to an implant within the eye raises a host of practical issues. Furthermore, both electrical and chemical stimulation, as used in known retinal prostheses, do not stimulate neural cells in a naturally occurring manner, which raises concerns about the long-term viability of such prostheses.

Accordingly, it would be an advance in the art to provide a retinal prosthesis which does not require an external supply and which stimulates neural cells in a more natural manner than electrical or chemical stimulation.

SUMMARY

The present invention provides an interface for selective excitation of a biological neural network. The interface includes a microelectromechanical (MEMS) device having a deformable membrane, and a tactile-sensitive neural cell disposed on the deformable membrane. The cell on the deformable membrane senses motion or deformation of the membrane and provides a signal, responsive to membrane motion or deformation, to the biological neural network. Preferably, the deformable membrane and cell have about equal areas, to provide selective excitation. An interface array including at least two such interfaces is also provided. A preferred embodiment of the invention is a retinal prosthesis interface array having, in each element of the array, a photodiode within the MEMS device for electrostatically actuating the deformable membrane. In this embodiment, the cells and deformable membranes are preferably transparent.

An advantage of the present invention is that a low level of light is required for membrane deflection. This allows a retinal neural prosthesis to operate at ambient levels of light with or without an external power supply and with a total number of pixels of up to 100,000 pixels within a 3 mm×3 mm chip. Another advantage is that the retinal prosthesis provides a natural and thus sustainable mechanism of cellular excitation, namely mechanical deformation of tactile sensors. Still another advantage is that the retinal prosthesis allows for good visual acuity (i.e. spatial resolution). More specifically, pixel sizes can be on the order of 10-20 microns, geometrically corresponding to visual acuity of 20/40-20/80, respectively.

DETAILED DESCRIPTION

Figure 1:
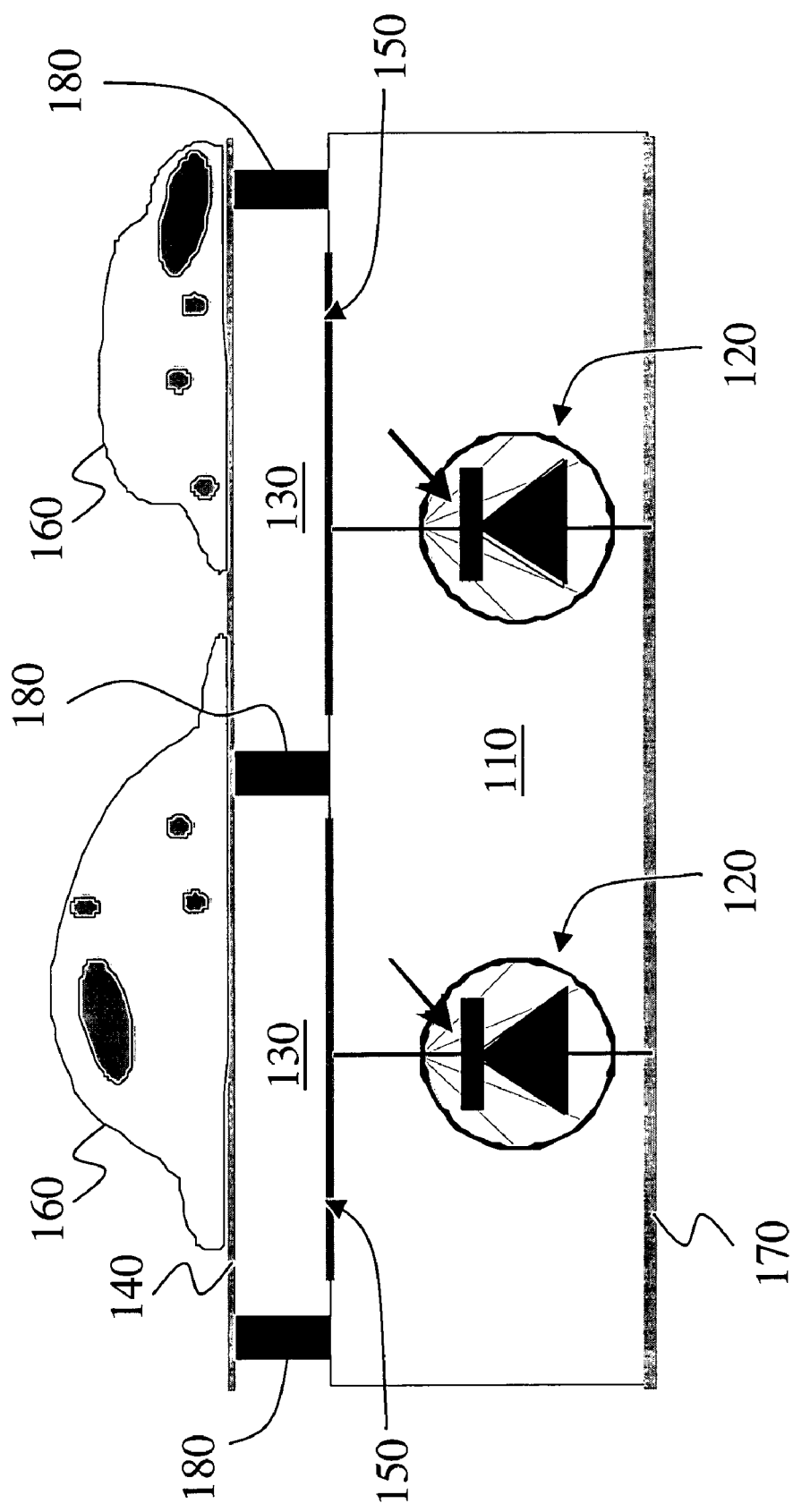
FIG. 1 shows an example of an interface according to the present invention.

FIG. 1 shows an example of an interface according to the present invention, having a deformable membrane 140. The interface of the example of FIG. 1 is a retinal prosthesis. Deformable membrane 140 is part of a MEMS device which, in this example, also includes a photodiode 120 and an electrode 150. Membrane 140 is separated from electrode 150 by a spacer 180. Typically, spacer 180 defines independent segments of an interface array. For example, FIG. 1 shows two such segments. Photodiodes 120 are included in a substrate layer 110. Substrate layer 110, membrane 140 and spacer 180 define open chambers 130. Open chamber 130 can be several microns wide. Deformable membrane 140 is separated from electrodes 150 by a gap on the order of microns. Preferably, this gap is about 1 micron. Deformable membrane 140 is flexible, and is preferably electrically conductive. Standard MEMS technology is suitable for providing the structure and dimensions shown on FIG. 1 (except cells 160), and this fabrication approach is preferred to reduce cost.

The interface of FIG. 1 includes one or more tactile-sensitive neural cells 160 disposed on deformable membrane 140. Cells 160 may be grown on membrane 140, attracted to membrane 140, or may be positioned on membrane 140 after growth or harvesting. Cells 160 are capable of making one or more synaptic connections to neural cells in a retina (e.g., bipolar or ganglion cells). These synaptic connections can be initiated or grown from cells 160 to retinal neural cells, or from retinal neural cells to cells 160 (i.e., these synaptic connections can be made in either direction). Alternatively, cells 160 can be retinal cells attracted to membrane 140 and adhered to its surface. In this case, cells 160 are synaptically connected to the biological neural network prior to being attached to membrane 140.

Cells 160 generate signals upon deformation by deformable membrane 140. Suitable cells for cells 160 include specialized touch sensor cells or tactile sensors as well as any type of neural cell that has a degree of tactile sensitivity. Furthermore, the signals generated by cells 160 are preferably strong enough to propagate further to the corresponding cells and axons in the retina that are synaptically connected to cells 160. The propagation eventually goes into the optic nerve and the visual cortex of the brain.

Power is preferably provided to photodiodes 120 with a power supply line 170 disposed on a surface of substrate layer 110 facing away from cells 160. Preferably, power supply line 170 is common to all photodiodes 120.

Figure 2:
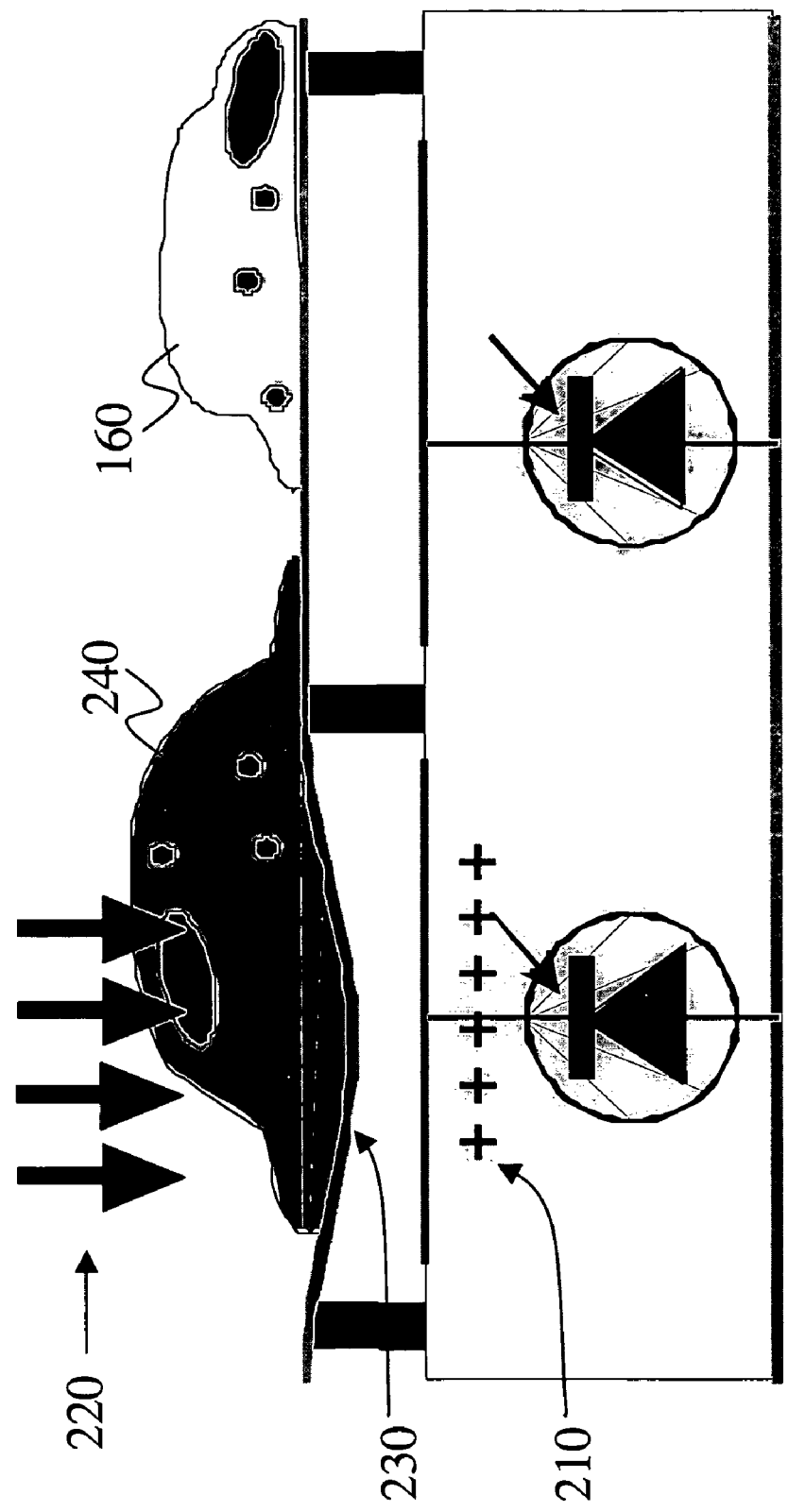
FIG. 2 shows an example of light penetrating through the cells and membrane to reach a photodiode. Cells sitting on top of an illuminated segment, being deformed, are excited.

FIG. 2 shows operation of the example of FIG. 1. A localized illumination 220 is received by one of photodiodes 120, which leads to the presence of a voltage 210 on electrode 150. As indicated above, voltage 210 is on the order of volts (i.e., about 1-20 volts). Voltage 210 electrostatically deforms membrane 140 to a deformed position 230, thus stimulating cell 240. In turn, cell 240 selectively stimulates the biological network it is connected to (i.e., the retina, in this example). Cell 160 in an adjacent segment which is not illuminated is substantially not stimulated. Thus, the stimulation provided by the present invention is selective.

In this embodiment, pulsed operation is preferable to reduce power consumption. When a pulse is applied to power supply line 170, voltage 210 is developed across the gap separating electrode 150 from membrane 140, and this voltage depends on the local light intensity received by photodiodes 120, as shown on FIG. 2. This locally varying pulsed gap voltage provides a locally varying pulsed deformation of membrane 140, which in turn provides selective pulsed stimulation of cells 160.

Pulsed excitation of cells 160 will be perceived as a continuous visual input provided the interval between pulses is short enough. This persistence of vision phenomenon is also exploited in standard television and video applications. Suitable pulse durations are between about 0.01 ms and about 10 ms, as known in the art, and suitable repetition rates are between about 25 Hz and about 80 Hz. Since cellular recovery time after stimulation is on the order of 10-20 ms, such a repetition rate is perceived as continuous or nearly continuous illumination.

Since the interface of FIG. 1 is a retinal prosthesis, light must be able to reach photodiodes 120. Preferably, illumination is from above on FIG. 1, and in this case, cells 160, deformable membrane 140 and electrode 150 are all preferably transparent. Alternatively, illumination can be from below on FIG. 1, and in this case power supply line 170 is preferably transparent. Power is preferably supplied to photodiodes 120 with an intra-ocular power supply, e.g., as disclosed in U.S. patent application Ser. No. 10/741,941. Alternatively, an external power supply can be used.

Figure 3:
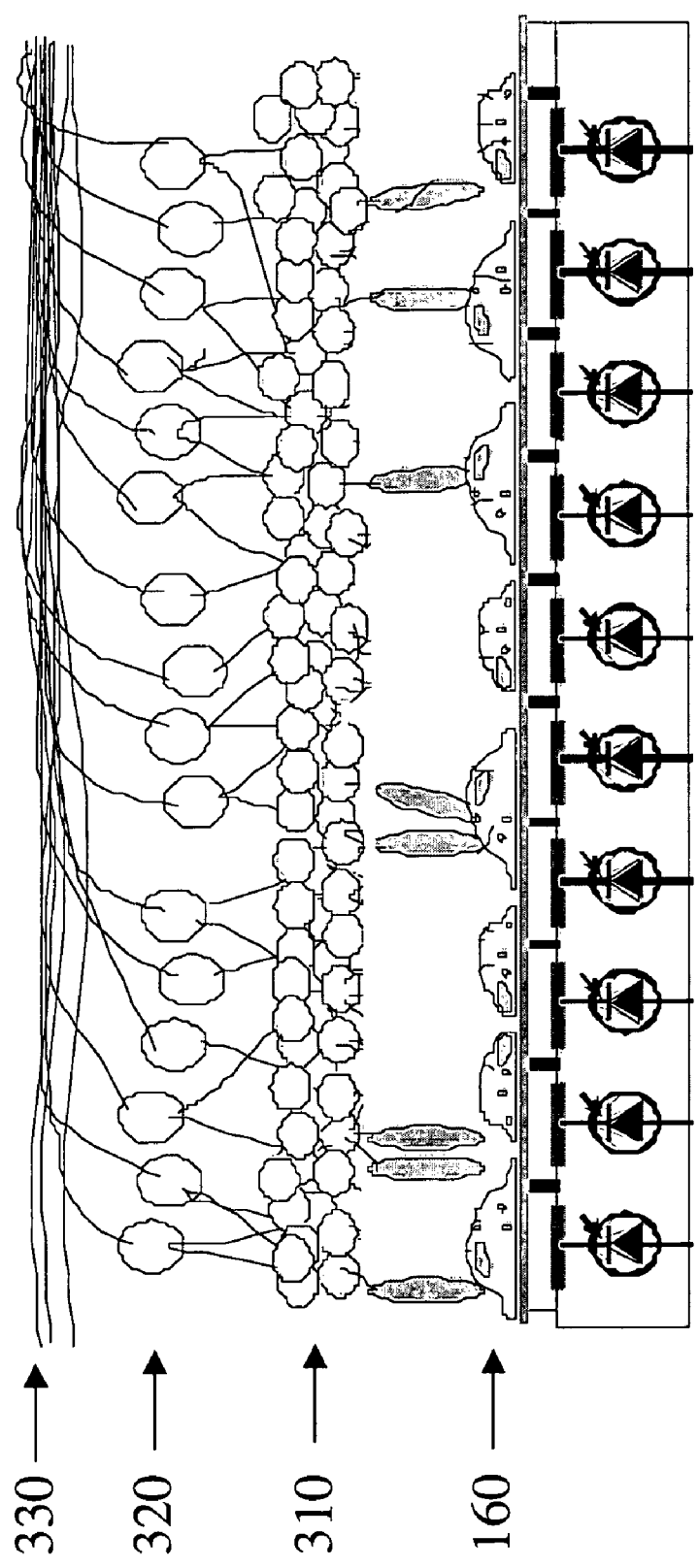
FIG. 3 shows an interface according to the present invention positioned under a retina with a diseased layer of photoreceptors.

FIG. 3 shows a retinal prosthesis according to the present invention and disposed sub-retinally (i.e., between the retina and the outermost layers of the eye). Cells 160 are in proximity to inner nuclear layer cells 310 (e.g., bipolar cells), which are connected to ganglion cells 320. Ganglion cells 320 are connected to axons 330 which transmit signals to the visual cortex via the optic nerve. Once cells 160 and cells 310 are positioned in proximity, as shown on FIG. 2, natural physiological processes can lead to the formation of synaptic connections between cells 160 and cells 310. Alternatively or in addition, growth of cellular processes and/or formation of synaptic connections between cells 160 and cells 310 can be stimulated, e.g. by adding a growth factor for a limited period of time. Alternatively, bipolar or ganglion retinal cells can be attracted to membrane 140, and migrate and adhere to membrane 140 while preserving synaptic connections between migrated cells and the retina.

Figure 4:
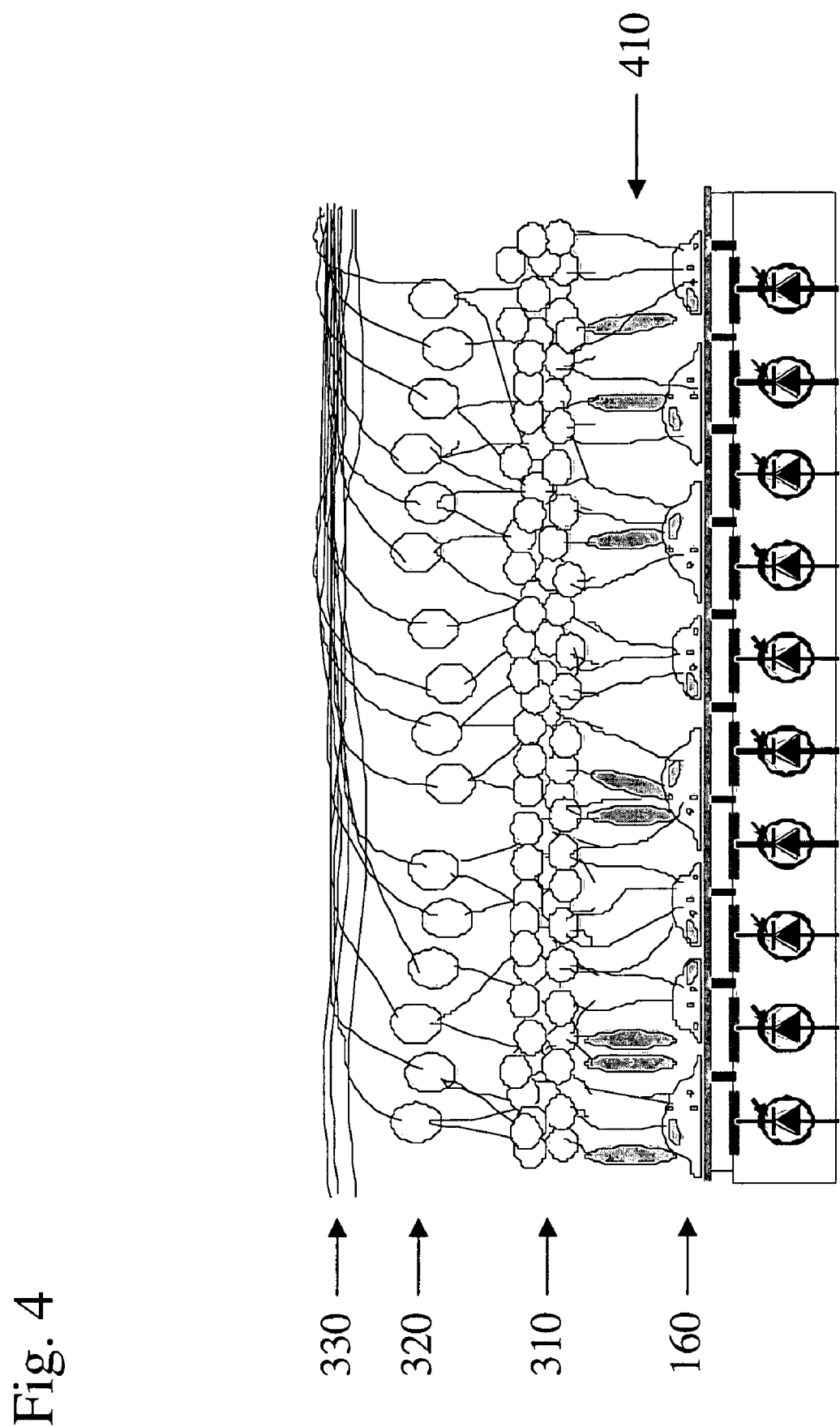
FIG. 4 shows an example of an interface according to the present invention with tactile cells creating synaptic connections with bipolar cells in a retina.

FIG. 4 shows a retinal prosthesis according to the present invention and disposed sub-retinally, after the formation of synaptic connections 410 between cells 160 and cells 310.

Figure 5:
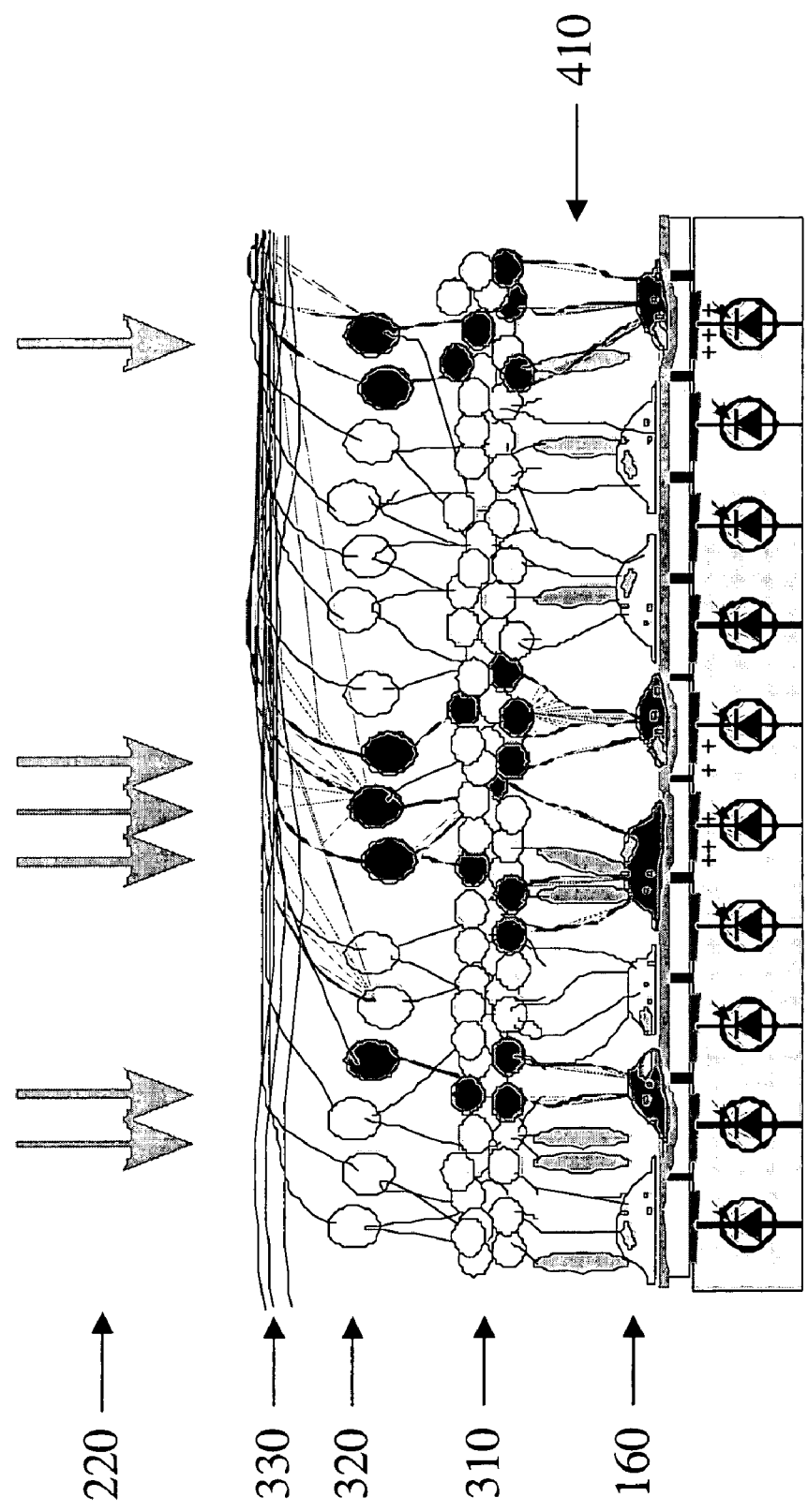
FIG. 5 shows an example of light illuminating several segments of the interface of FIG. 4.

FIG. 5 shows operation of the example of FIG. 4. Illumination 220 is received by photodiodes 120 in some segments of the interface array. Cells 160 above illuminated photodiodes 120 are stimulated by motion of deformable membrane 140. The stimulation of cells 160 is transmitted via synaptic connections 410 to inner nuclear layer cells 310, which transmit the stimulation to ganglion cells 320 and thence to axons 330 and the visual cortex of the brain.

Some basic performance parameters of the example of FIGS. 1-5 can be estimated as follows. Membrane 140 and electrode 150 form a capacitor having a capacitance of about $C=1$ fF, assuming a 1 µm gap between electrode 150 and membrane 140 having lateral dimensions of 10 µm by 10 µm. For electrostatic deflection of membrane 140 in this example, a voltage on the order of $U=10V$ is required. The energy required to charge this capacitor to $U=10$ V is $E=CU^2/2=50$ fJ. Assuming an image refreshing rate of 100 Hz, the required power per segment is only $P=5$ pW, and for pixel density of 10,000 pixels/mm$^2$, the required power will be 50 nW/mm$^2$.

A typical power flux on the retina (e.g. outdoors during daytime) is about 900 nW/mm$^2$. If about 30% of this light is converted into electricity, the electric power density will be 300 nW/mm$^2$. This power flux is more than sufficient to power a pixel density of 10,000 pixel/mm$^2$, which geometrically corresponds to a visual acuity of 20/40. To discharge a capacitor after termination of illumination a resistance across each capacitor should be $R=t/C$, i.e. $R=1/(100$ Hz$\cdot 1$fF$)=10^{13}$ Ohm, corresponding to a time constant t of 10 ms.

The above detailed description is by way of example, not limitation. Thus many variations of the above embodiments are within the scope of the present invention.

For example, the above embodiments relate to stimulation of a retinal neural network. The invention can also be used to stimulate any kind of biological neural network, including but not limited to: central nervous system (CNS) neural networks (e.g., brain cortex), nuclei within the CNS, and nerve ganglia outside the CNS. A biological neural network is made up of interconnected biological processing elements (i.e., neurons) which respond in parallel to a set of input signals given to each.

Another variation is to harvest cells 160 from the same patient (e.g., from the patient's skin) in which the interface of the present invention is implanted, thereby avoiding rejection of cells 160 by making them autologous. Tactile sensitivity is inherent property of many types of neural cells and not only of specialized tactile sensor cells, thus other neural cells might be used for this purpose as well.

Yet another variation is a pulsed contacting mode. In this pulsed contacting mode membrane 140 can touch electrode 150. This contact will discharge the capacitor formed by membrane 140 and electrode 150, and then membrane 140 will then return to its original position (as on FIG. 1). If light continues to illuminate photodiode 120, this process of charging the capacitor, deflection of a membrane, and discharge will continue cyclically. The repetition rate of such a process will depend on the intensity of the light as well as on geometrical and mechanical properties of membrane 140.

Another variation is epi-retinal (i.e., between the retina and the vitreous humor) disposition of a retinal prosthesis, as opposed to the sub-retinal disposition shown in FIGS. 3-5. In this variant, cells 160 preferably make synaptic connections to ganglion cells 320.

Still another variation is to perform optical sensing remotely and use electrical signals from the remote optical sensor to drive an interface according to the present invention. In other words, the invention can be practiced, even for a retinal prosthesis, without performing optical to electrical conversion within the prosthetic implant.

What is claimed is:

1. An interface to a biological neural network, the interface comprising:
   a) a microelectromechanical (MEMS) device including a deformable membrane; and
   b) a tactile-sensitive neural cell disposed on said deformable membrane;
   wherein said neural cell provides a signal to said biological neural network responsive to deformation or motion of said membrane.

2. The interface of claim 1, wherein said neural cell and said deformable membrane have about equal areas.

3. The interface of claim 1, wherein said deformable membrane has an area less than about 1000 square microns.

4. The interface of claim 1, wherein said interface is implanted within a patient and wherein said neural cell is a cell harvested from said patient.

5. The interface of claim 1, wherein said neural cell comprises a specialized touch sensor cell.

6. The interface of claim 1, wherein said neural cell is synaptically connected to said biological neural network.

7. The interface of claim 1, wherein said biological neural network comprises a retina.

8. The interface of claim 7, wherein said interface is disposed subretinally relative to said retina.

9. The interface of claim 7, wherein said interface is disposed epi-retinally relative to said retina.

10. The interface of claim 1, wherein said deformable membrane is capable of being electrostatically actuated by an electrode separated from said membrane by a gap.

11. The interface of claim 10, wherein said gap is about 1 micron.

12. The interface of claim 10, wherein said MEMS device further comprises a photodiode.

13. The interface of claim 12, wherein said deformable membrane is transparent.

14. The interface of claim 12, wherein said neural cell is transparent.

15. The interface of claim 12, wherein said deformable membrane can make contact with said electrode when said photodiode is illuminated, whereby pulsed tactile stimulation of said neural cell is provided.

16. The interface of claim 12, further comprising a pulsed power supply connected to said MEMS device.

17. An interface array comprising a plurality of interfaces according to claim 1.

18. The interface of claim 1, wherein said interface is implanted within a patient and wherein said neural cell is a cell migrated from said patient.

* * * * *